United States Patent [19]

Tovey et al.

[11] Patent Number: 5,450,842
[45] Date of Patent: Sep. 19, 1995

[54] ENDOSCOPIC SURGICAL RETRACTOR

[75] Inventors: H. Jonathan Tovey, Milford; Douglas J. Cuny, Bethel, both of Conn.

[73] Assignee: United States Surgical Corporation, Norwalk, Conn.

[21] Appl. No.: 20,342

[22] Filed: Feb. 19, 1993

[51] Int. Cl.$^6$ ............................................. A61B 19/00
[52] U.S. Cl. .................................... 600/206; 606/1; 600/204; 600/226
[58] Field of Search ............... 128/20, 657, 772, 3; 604/95, 264, 280–282; 606/1, 78, 190–198

[56] References Cited

U.S. PATENT DOCUMENTS

| | | | |
|---|---|---|---|
| 2,118,631 | 5/1938 | Wappler | 604/170 |
| 3,503,385 | 3/1970 | Stevens | 128/657 |
| 3,620,212 | 11/1971 | Fannon, Jr. et al. | |
| 3,782,381 | 1/1974 | Winnie | 604/281 |
| 3,796,211 | 3/1974 | Kohl | 604/281 |
| 3,890,977 | 6/1975 | Wilson. | |
| 3,957,055 | 3/1976 | Linder et al. | 606/108 |
| 4,402,684 | 9/1983 | Jessup | 604/282 |
| 4,665,906 | 5/1987 | Jervis. | |
| 4,895,168 | 1/1990 | Machek | 128/772 |
| 5,037,178 | 8/1991 | Stoy et al. | |
| 5,055,101 | 10/1991 | McCoy | 604/95 |
| 5,106,369 | 4/1992 | Christmas. | |
| 5,109,830 | 5/1992 | Cho | 128/772 |
| 5,113,846 | 5/1992 | Hiltebrandt et al. | 128/20 |
| 5,122,155 | 6/1992 | Eberbach. | |
| 5,125,902 | 6/1992 | Berry et al. | 604/164 |
| 5,143,085 | 9/1992 | Wilson | 128/772 |
| 5,170,787 | 12/1992 | Lindegren | 128/772 |
| 5,188,111 | 2/1993 | Yates et al. | 606/78 |
| 5,259,377 | 11/1993 | Schroeder | 604/95 |

FOREIGN PATENT DOCUMENTS 0530595  3/1993  European Pat. Off. ............ 606/108

OTHER PUBLICATIONS

"Development of Polymeric Shape Memory Material", Shirai et al., Dec. 1988.
"Shape Memory Polymer", Mitsubishi Heavy Industries America, 1992.
"Processing Instructions for Mitsubishi Shape Memory Polymer", Manual No. 1, Rev. 2.2, Mitsubishi Heavy Industries, Ltd., Apr. 1992.
"Tinel ® Shape-Memory Alloys", Raychem Corporation, May 1989.
"Shape Memory Metal", Raychem Corporation, Jul. 1984.
"Designing With The Shape Memory Effect", Duerig et al., MRS Int'l. Mtg. on Adv. Mats., vol. 9, 1989.

Primary Examiner—Stephen C. Pellegrino
Assistant Examiner—Glenn Dawson

[57] ABSTRACT

The invention described herein provides a surgical apparatus for use in endoscopic or laparoscopic procedures having a tubular body portion with a first substantially tractable section and a second substantially firm section, and a rod member disposed at least partially within the tractable section of the tubular body portion and movable between a deformed position and a preformed position wherein the first section defines structure which is dimensioned and configured for effectuating retraction.

32 Claims, 5 Drawing Sheets

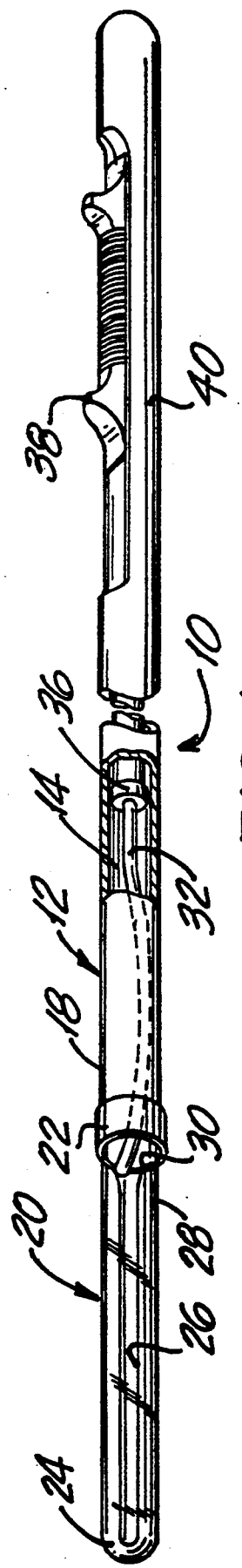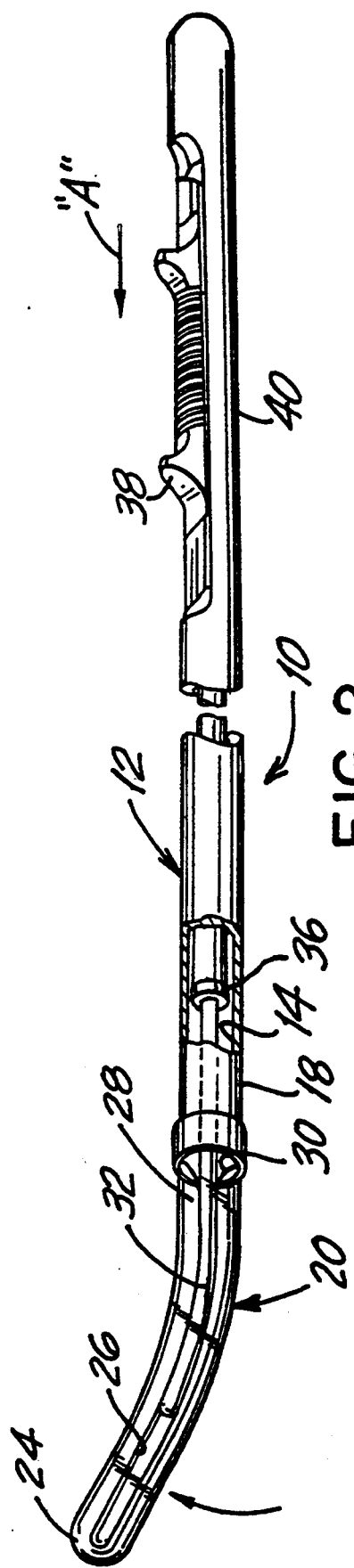

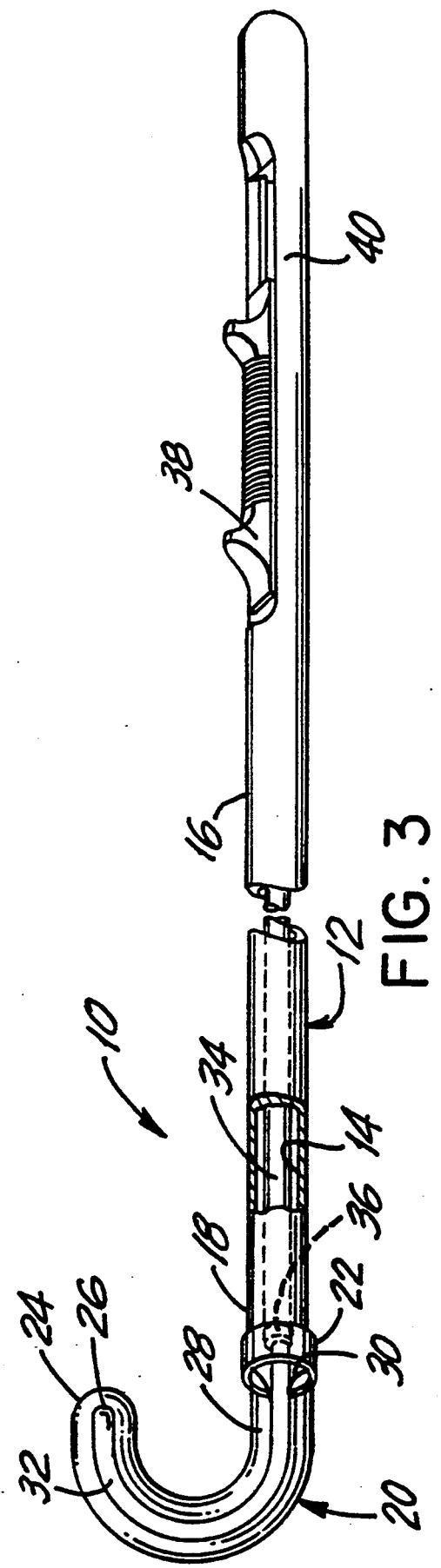

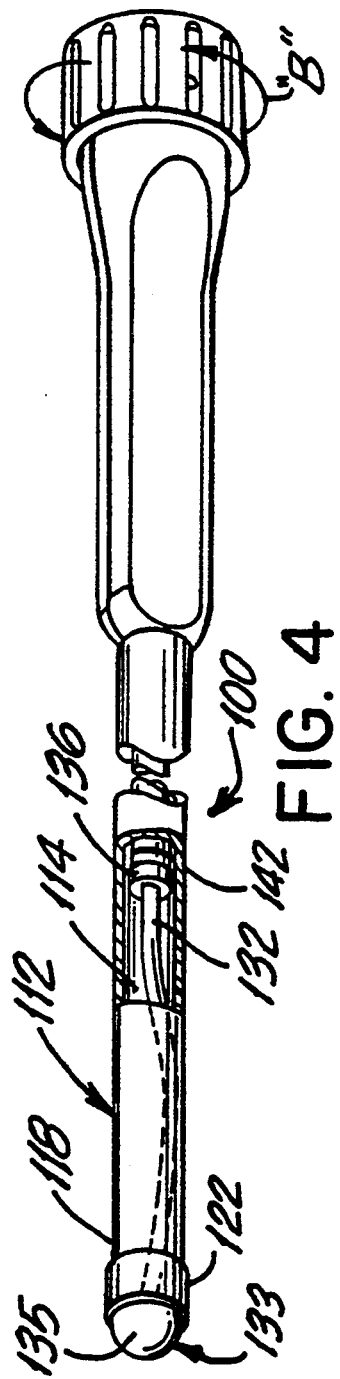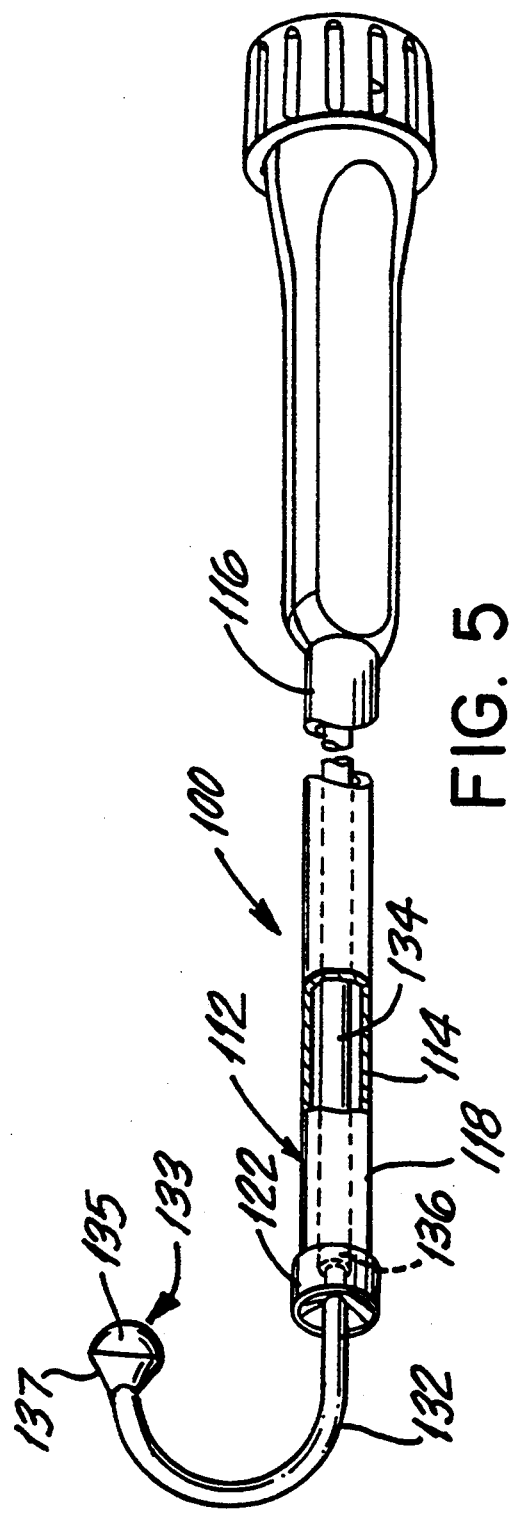

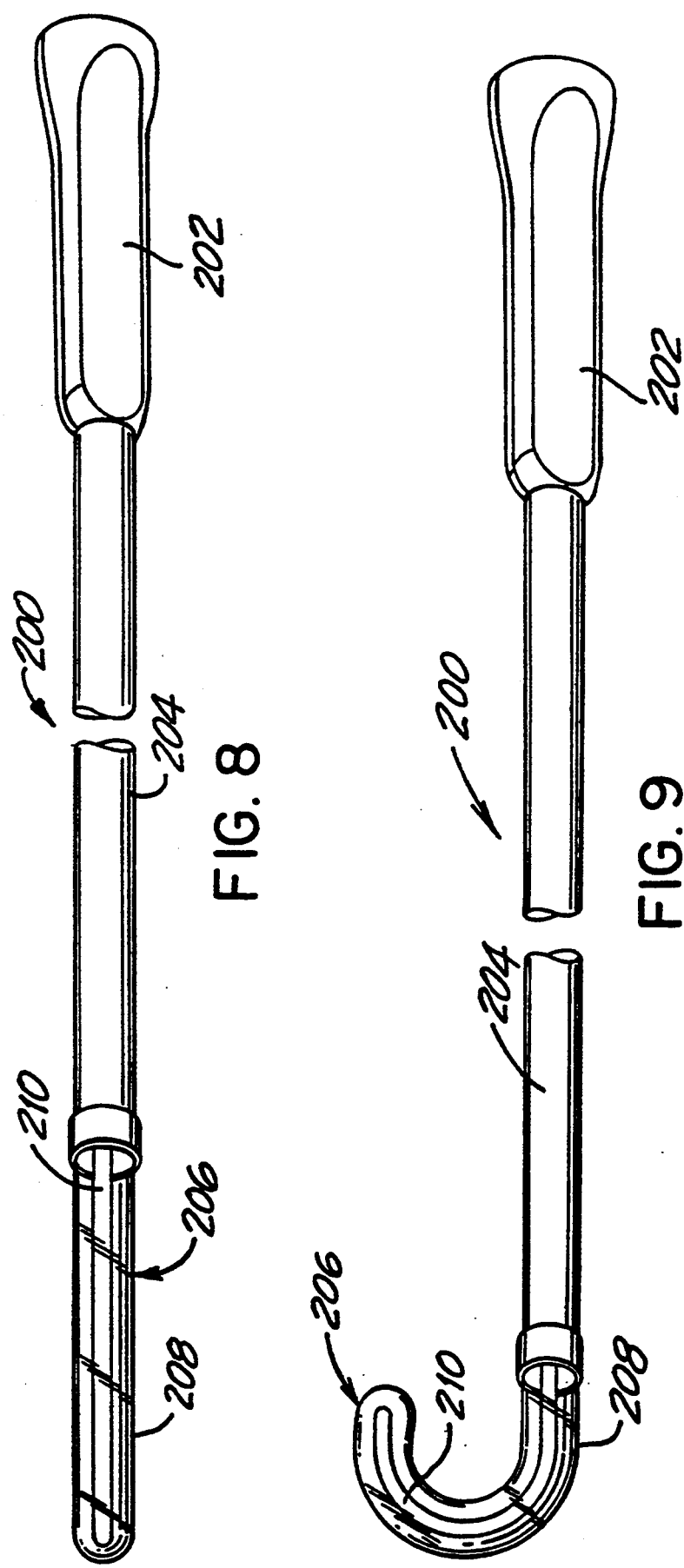

ENDOSCOPIC SURGICAL RETRACTOR

BACKGROUND OF THE INVENTION

1. Field of the Invention

This invention relates to surgical retractor apparatus, and more particularly, to apparatus for retracting organs or body tissue during endoscopic or laparoscopic surgical procedures.

2. Description of Related Art

In laparoscopic and endoscopic procedures, surgery is performed through a small incision made in the patient's body, generally to provide access for a trocar or cannula device. Once extended into the patient's body, the cannula device permits insertion of a variety of surgical instruments including scissors, graspers, and staplers.

Surgical retractors for use in endoscopic and laparoscopic surgical procedures are also known in the art. However, prior art endoscopic retractors are often inherently limited in their ability to effect retraction of large organs. This limitation results from the fact that the operative surface area of the retractor portions of many of these instruments is limited by the diameter of the trocar or cannula device through which the instrument must pass to be introduced to the operative site. In the past, this limitation has been overcome through the use of mechanical linkages having a plurality of moving parts which expand the surface area of the retractor portion once the instrument has been extended through the cannula device. However, instruments having linkage assemblies are often expensive to manufacture.

Therefore, it is an object of the subject invention to provide a surgical retractor for use in endoscopic or laparoscopic procedures having a variably configurable operative surface area.

It is another object of the subject invention to provide a surgical retractor for use in endoscopic and laparoscopic procedures which is inexpensive to manufacture.

It is another object of the subject invention to provide a surgical retractor for use in endoscopic or laparoscopic procedures which has a minimum number of external moving parts.

It is yet another object of the subject invention to provide a surgical retractor for use in endoscopic or laparoscopic procedures having a substantially atraumatic retractor portion.

These and other objects of the surgical apparatus of the subject invention will become more readily apparent from the following derailed description of the invention.

SUMMARY OF THE INVENTION

A novel surgical apparatus is provided for performing retraction tasks during endoscopic or laparoscopic procedures. The apparatus comprises a tubular member having a first substantially tractable section and a second substantially firm section. A reciprocal rod member having a preformed configuration is disposed at least partially within the tubular member and is movable in a longitudinal direction between a retracted position spaced from the first section and a fully protracted or extended position disposed within the first section. In operation, movement of the reciprocal rod member between the retracted and protracted positions causes the tractable section of the tubular member to conform to the preformed configuration of the reciprocal rod member.

The apparatus of the subject invention further comprises actuation means for remotely moving the reciprocal rod member relative to the tubular member. Preferably, the actuation means includes an elongated axial control shaft extending through the tubular member and having an actuator disposed at the proximal end thereof for user manipulation and having a coupling at the distal end thereof for mounting the reciprocal rod member thereto. In a preferred embodiment of the subject invention, the first section of the tubular member is formed of a thermoplastic material having a glass transition temperature in the range of about 20° C. to 40° C. Preferably, the first section of the tubular member is formed of polyurethane having a glass transition temperature of 30° C. The reciprocal rod member is preferably formed of a super elastic material such as a shape memory alloy. These alloys may be deformed by an applied stress and then return toward an original shape or configuration once the stress is released.

In another embodiment of the subject invention, a surgical apparatus is provided which comprises a first substantially tractable section and a second substantially firm section. A stationary rod member having a preformed configuration is disposed in the tubular member and is movable between a deformed position in which the first section of the tubular member is substantially elongated and a preformed position in which the first section of the tubular member conforms to the preformed configuration of the rod member when the instrument is introduced into the operative site.

In yet another embodiment of the subject invention, a surgical apparatus is provided which comprises an elongated tubular body, and a retractor member preferably formed of a super elastic material which is disposed at least partially within the tubular body. The retractor member is movable between a deformed retracted position internal of the tubular body and a relaxed protracted or extended position external of the tubular body. An atraumatic nose piece may be provided at a distal end of the retractor member for abutting against a distal end of the tubular body when the retractor member is in the protracted position. Actuation means are also provided for remotely moving the retractor member between the retracted position and the protracted position. In addition, sealing means may be provided for inhibiting the egress of insufflation gas through the body portion of the apparatus.

The provision of retractor members configured in various unstressed shapes is within the scope of the present invention. For example, the unstressed shape of the retractor rod may define a substantially circular formation, or an angularly depending formation. Moreover, it is envisioned that the tubular body portion of the surgical apparatus of the subject invention may be adapted to receive various removable retractor rod members each having a distinct unstressed configuration. Accordingly, the apparatus may be provided as a kit having a tubular body portion and a plurality of removable retractor rod members each having a distinct unstressed configuration and adapted to be easily introduced into the tubular body portion of the instrument as dictated by the needs of the user and the retraction task at hand.

Further features of the subject invention will become more readily apparent from the following detailed description of the invention taken in conjunction with the drawings.

BRIEF DESCRIPTION OF THE DRAWINGS

Preferred embodiments of the subject invention are described hereinbelow with respect to the drawings wherein:

FIG. 1 is a perspective view of a surgical apparatus in accordance with a preferred embodiment of the subject invention with the retractor portion thereof in a retracted position;

FIG. 2 is a perspective view of the surgical apparatus of FIG. 1 with the retractor portion thereof in a partially protracted position;

FIG. 3 is a perspective view of the surgical apparatus of FIG. 1 with the retractor portion thereof in a fully protracted position;

FIG. 4 is a perspective view of another surgical apparatus in accordance with a preferred embodiment of the subject invention with the retractor portion thereof in a retracted position;

FIG. 5 is a perspective view of the surgical apparatus of FIG. 5, with the retractor portion thereof in an extended position;

FIG. 8 is a perspective view of yet another surgical apparatus in accordance with a preferred embodiment of the subject invention with the retractor portion thereof in a first position; and FIG. 9 is a perspective view of the surgical apparatus of FIG. 8 with the retractor portion thereof in a second position.

DETAILED DESCRIPTION OF THE PREFERRED EMBODIMENTS

Figure 6:
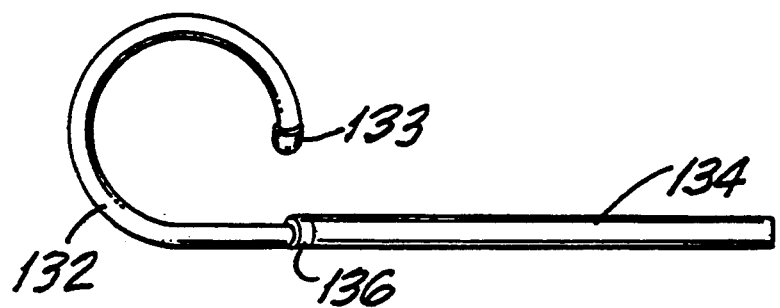
FIG. 6 is a perspective view of another embodiment of the retractor portion of the apparatus of FIG. 4 removed from the body of the instrument.

Because endoscopic procedures are more common than laparoscopic procedures, the present invention shall be discussed in terms of endoscopic procedures and apparatus. However, use herein of terms such as "endoscopic", "endoscopically", and "endoscopic portion", among others, should not be construed to limit the present invention to an apparatus for use only in conjunction with an endoscopic tube. To the contrary, it is believed that the present invention may find use in procedures wherein access is limited to a small incision including but not limited to laparoscopic procedures.

In the drawings and in the description which follows, the term "proximal", as is traditional, will refer to the end of the apparatus which is closest to the operator, while the term "distal" will refer to the end which is furthest from the operator.

Referring now in detail to the drawings, wherein like reference numerals identify similar elements, a surgical apparatus for performing retraction tasks during endoscopic or laparoscopic procedures in accordance with a preferred embodiment of the subject invention is illustrated in FIG. 1 and is designated generally by reference numeral 10. Surgical apparatus 10 comprises an elongated tubular body portion 12 defining an axial passageway 14 which extends from the proximal end 16 of body portion 12 to the distal end 18 thereof. Body portion 12 is preferably formed of a firm, lightweight, plastic material such as, for example, LEXAN brand material which is marketed by General Electric Corporation.

A substantially tractable retractor section 20 is mounted at the distal end 18 of body portion 12 by an annular mounting collar 22. Alternatively, retractor section 20 may be monolithically formed with body portion 12. Retractor section 20 has an atraumatic tip portion 24 at the distal end thereof and an axial cavity 26 extends partially therethrough from the proximal end 28 thereof. The cross-sectional diameters of retractor section 20 and tubular member 12 are substantially equal and are suitably dimensioned for endoscopic utilization. Retractor section 20 is preferably formed of a thermoplastic material having a glass transition temperature in the range of about 20° C. to 40° C. It is within this temperature range that the internal body temperature of most warm blooded animals lie. The specific glass transition temperature of the material from which retractor section 20 is formed however, will depend upon the subject being operated on. For example, in veterinary procedures, the preferred glass transition temperature of the material will differ from that which is preferred in surgical procedures involving human subjects. Preferably, for surgical procedures involving human subjects the material from which retractor section 20 is formed is polyurethane having a glass transition temperature of about 30° C. Therefore, at temperatures above about 30° C. (i.e. inside the patient's body), the polyurethane material from which retractor section 20 is formed will exhibit elastic or spring-like attributes. Conversely, at temperatures below about 30° C. (i.e. outside the patient's body), retractor section 20 will remain rigid or glassy. The benefits of this thermoplastic material will become more readily apparent from the discussion which follows.

The entry 30 to the axial cavity 26 formed in retractor section 20 is inwardly tapered to define a guideway for assisting the entry of a reciprocal rod member 32 into axial cavity 26 from an undeployed retracted position substantially within the axial passageway 14 of body portion 12. Reciprocal rod member 32 is preferably formed from a material having a preformed configuration which can be deformed under stress and which returns to its preformed configuration when the stress is released. An example of a material which satisfies this requisite characteristic is a shape memory alloy (such a material, composed of nickel and titanium, is available from Raychem Corp. under the trade name TINEL). Thus, when reciprocal rod member 32 is in an undeployed position disposed within passageway 14 of body portion 12, it is in a stressed condition restrained by the walls of tubular body portion 12. The proximal end of reciprocal rod member 32 is mounted to a control shaft 34 at a connective end portion 36 thereof. Control shaft 34 extends longitudinally through axial passageway 14 and is configured for longitudinal translation with respect to body portion 12. A slide actuator 38 which is associated with handle portion 40 is interconnected to the proximal end of control shaft 34 for facilitating remote user actuation of apparatus 10.

In use, the apparatus may be introduced into the abdominal cavity of a patient through an incision or, alternatively, through a trocar or cannula device (not shown) which is inserted into a small incision in the patient's body. Because retractor section 20 remains substantially firm at room temperature, its insertion through the trocar or cannula device is smooth and unobstructed. However, once extended into the abdomen, the thermoplastic material from which retractor section 20 is formed, advantageously becomes tractable. As explained hereinabove, the change in rigidity of retractor section 20 is due to the relationship between the glass transition temperature of the material and the body temperature of the patient. Accordingly, once introduced to the operative site, the patient's body temperature, which is preferably above the glass transition temperature of the material, causes retractor section 20 to become flexible and suitable for conforming to the preformed shape of rod member 32.

In operation, by exerting an axially applied force upon actuator 38 in the direction indicated by arrow "A" in FIG. 2, control shaft 34 is urged in a distal direction, driving the reciprocal rod member 32 forward. Initially, the distal end of reciprocal rod member 32 is guided into the axial cavity 26 of retractor portion 20 by the tapered entry 30 defined therein. Alternatively, in instances where the distal end portion of the rod member is substantially linear in configuration, the rod member may be initially extended at least partially into the axial cavity 26 of retractor portion 20 prior to its introduction to the operative site.

Referring to FIG. 2, as the reciprocal rod member 32 extends into axial cavity 26, it gradually deploys into its preformed configuration, moving from its stressed position of FIG. 1 to an unstressed relaxed position as it is liberated from the restraint of the rigid walls of tubular body portion 12. Consequently, the tractable retractor section 20 of surgical apparatus 10 may be variably formed into a plurality of intermediate configurations as the retractor rod 32 is gradually extended into the axial cavity 26 thereof. In deploying retractor rod 32, sufficient rigidity is instilled in the tractable retractor section 20 of surgical apparatus 10 to effectuate retraction of large organs and body tissue.

Preferably, as illustrated in FIG. 3, the preformed shape of reciprocal rod member 32 is substantially U-shaped in configuration such that, when fully deployed, the distal end portion of the instrument 10 defines a generally J-shaped atraumatic retractor mechanism suitable for manipulating large organs or body tissue during endoscopic or laparoscopic surgical procedures. Other retractor configurations are envisioned, including, for example, a retractor defining a substantially continuous loop (see generally, FIG. 6), or one which extends substantially angularly from the longitudinal axis of the instrument (see generally, FIG. 7).

Turning now to FIGS. 4 and 5, another surgical apparatus in accordance with a preferred embodiment of the subject invention is illustrated and is designated generally by reference numeral 100. Surgical apparatus 100 comprises a tubular body portion 112 having an elongated passageway 114 extending therethrough from a proximal end 116 to a distal end 118 thereof.

A retractor member 132 is associated with body portion 112 and is movable with respect thereto between an undeployed position enclosed within the passageway 114 of body portion 112, and a deployed position extending at least partially from the distal end 118 of body portion 112. Retractor member 132 is formed of a material having a desired preformed configuration which may be deformed under stress and which returns to its preformed shape once the stress is released. Preferably, retractor member 132 is formed of a shape memory alloy, such as TINEL brand material, and has a substantially J-shaped configuration in its unstressed condition shown in FIG. 5. An atraumatic nose piece 133 having a substantially hemi-spherical distal portion 135 and a frusto-conical shaped proximal end portion 137, is provided at the distal end of retractor member 132. In the retracted undeployed position of FIG. 4, wherein retractor member 132 is in a deformed condition restrained by the walls of tubular body portion 112, the frusto-conical shaped proximal end portion 137 of nose piece 133 is positioned within a correspondingly shaped seat 139 formed in the collar member 122 which is provided at the distal end 118 of body portion 112. The engagement of nose piece 133 within collar member 122 creates a streamlined structure which is easily inserted through an incision, a trocar, or cannula device and which inhibits the capture of tissue to avoid damage thereto. Retractor member 132 is mounted to the distal end of an axial control shaft 134 through a coupling 136. At least one seal member 142 is disposed within the tubular body portion of surgical apparatus 100 for inhibiting the egress of insufflation gas therethrough. A rotatable actuator 138 which is associated with handle portion 140 is connected to the proximal end of control shaft 134 for user actuation of surgical apparatus 100.

In operation, surgical apparatus 100 is inserted into an incision, a trocar, or cannula device with retractor member 132 in the deformed and undeployed position of FIG. 4. Once introduced into the abdominal cavity of the patient, the user may rotate actuator 138 in the direction indicated by arrow "B" to drive control shaft 134 forward. Thereupon, retractor member 132 gradually relaxes from its deformed stressed position as it deploys to its preformed unstressed J-shaped configuration of FIG. 5. At such a time, surgical apparatus 100 may be remotely manipulated by the user to effectively retract organs or body tissue within the patient's body.

Figure 7:
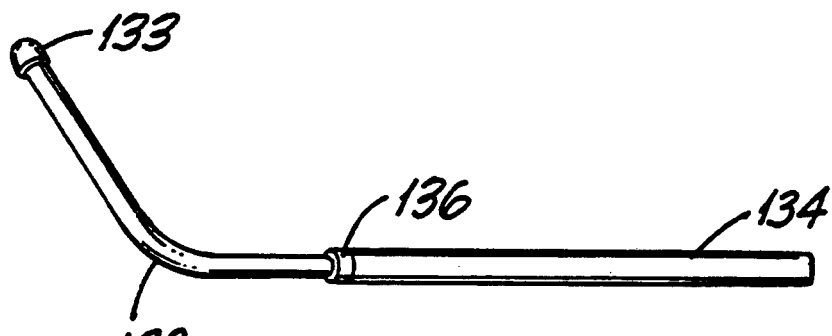
FIG. 7 is a perspective view of another embodiment of the retractor portion of the apparatus of FIG. 4 removed from the body of the instrument.

Referring now to FIGS. 6 and 7, alternative configurations of retractor rod 132 are illustrated, each of which is coupled to a removable control shaft 134 adapted to be selectively mounted within the tubular body portion 112 of the surgical apparatus 100 of the subject invention by the user. Selection of an appropriate retractor rod configuration will be dictated by the needs of the surgeon and the procedure to be performed. Accordingly, the subject invention may be provided as a kit which would include at least one tubular body portion 112, and at least two retractor rod members 132 of different configuration, each fitted to a respective control shaft 134 and adapted to be selectively mounted in the body portion 112 of the instrument.

Turning to FIGS. 8 and 9, yet another surgical apparatus in accordance with a preferred embodiment of the subject invention is illustrated and is designated generally by reference numeral 200. Surgical apparatus 200 comprises a handle portion 202, an elongated tubular body portion 204 extending from handle portion 202 and dimensioned for endoscopic utilization, and a retractor assembly 206 operatively associated with the distal end of tubular body portion 204. Retractor assembly 206 includes a substantially tractable outer tube portion 208 preferably formed of a thermoplastic material such as polyurethane having a glass transition temperature of about 30° C., and a stationary rod member 210 disposed coaxially within outer tube portion 208 and preferably formed of a shape memory alloy such as TINEL. Stationary rod member 210 preferably has a preformed J-shaped configuration although other configurations are envisioned.

In use, surgical apparatus 200 is introduced to the surgical site by passage through an incision, trocar, or cannula device, whereupon the body temperature of the patient effects the tractability of the thermoplastic material from which outer tube member 208 is formed, such that outer tube member 208 conforms to the preformed J-shaped configuration of rod member 210.

Although the surgical apparatus of the subject invention has been described with respect to a preferred embodiment, it is apparent that changes or modifications made be made thereto without departing from the spirit or scope of the invention as defined by the appended claims. To the extent not already indicated, it will also be understood by those of ordinary skill in the art that any of the various embodiments herein described and illustrated may be further modified to incorporate features shown in another of the embodiments.

What is claimed is:

1. A surgical apparatus comprising:
   a) a tubular member having a first substantially tractable section and a second substantially firm section and defining a longitudinal axis; and
   b) a rod member having a preformed configuration disposed at least partially within said second section of said tubular member and deformable between a deformed position wherein said first section is substantially in line with said second section and a preformed position wherein said rod member is disposed at least partially within said first section and said rod member causes said first section to conform to said preformed configuration of said rod member when said apparatus is introduced into a surgical site and said tractable section is heated within a predetermined temperature range, said rod member having a fixed longitudinal orientation with respect to said tubular member.

2. A surgical apparatus comprising:
   a) a tubular member having a first substantially tractable section and a second substantially firm section and defining a longitudinal axis;
   b) a rod member having a preformed configuration disposed at least partially within said second section of said tubular member and deformable between a deformed position wherein said first section is substantially in line with said second section and a preformed position wherein said rod member is disposed at least partially within said first section and said rod member causes said first section to conform to said preformed configuration of said rod member when said apparatus is introduced into a surgical site and said tractable section is heated within a predetermined temperature range, said rod member being configured for reciprocal longitudinal movement with respect to said tubular member; and
   c) means for remotely moving said rod member in a longitudinal direction with respect to said tubular member.

3. A surgical apparatus as recited in claim 2, wherein said first section of said tubular member is formed of a thermoplastic material.

4. A surgical apparatus as recited in claim 3, wherein said thermoplastic material has a glass transition temperature of between about 20° C. and 40° C.

5. A surgical apparatus as recited in claim 4, wherein said thermoplastic material is polyurethane having a glass transition temperature of about 30° C.

6. A surgical apparatus as recited in claim 2, wherein said rod member is formed of a super elastic material.

7. A surgical apparatus as recited in claim 6, wherein said superelastic material is a shape memory alloy.

8. A surgical apparatus comprising:
   a) a tubular member having a first substantially tractable section and a second substantially firm section and defining a longitudinal axis; and b) a reciprocal rod member having a preformed configuration disposed entirely within said tubular member and movable in a longitudinal direction between a deformed retracted position and a protracted position disposed at least partially within said first section, said rod member causing said first section to conform to said preformed configuration of said reciprocal rod member when said rod member is moved towards said protracted position.

9. A surgical apparatus as recited in claim 8, further comprising actuation means for remotely moving said reciprocal rod member relative to said tubular member.

10. A surgical apparatus as recited in claim 9, wherein said actuation means comprises an axial control shaft coupled to said reciprocal rod member and movable in a longitudinal direction with respect to said tubular member.

11. A surgical apparatus as recited in claim 8, wherein said first section of said tubular member is formed of a thermoplastic material.

12. A surgical apparatus as recited in claim 11, wherein said thermoplastic material has a glass transition temperature of between about 20° C. and 40° C.

13. A surgical apparatus as recited in claim 11, wherein said thermoplastic material is polyurethane having a glass transition temperature of about 30° C.

14. A surgical apparatus as recited in claim 8, wherein said reciprocal rod member is formed of a super elastic material.

15. A surgical apparatus as recited in claim 8, wherein said reciprocal rod member is formed of a shape memory alloy.

16. A surgical apparatus as recited in claim 8, wherein said first section has a substantially arcuate configuration when said reciprocal rod member is in said protracted position.

17. A surgical apparatus as recited in claim 8, wherein said first section of said tubular member has a diameter which is substantially equal to a diameter of said second section of said tubular member.

18. A surgical apparatus comprising:
   a) a tubular member having a tractable distal end portion and a substantially firm proximal portion and defining a longitudinal axis; and
   b) a reciprocal rod member having a preformed shape disposed entirely within said tubular member and remotely movable in a longitudinal direction between a retracted, stressed and deformed position spaced from said distal end portion of said tubular member and a protracted unstressed position disposed within said distal end portion, and wherein said rod member causes said distal end portion of said tubular member to conform to said preformed shape of said reciprocal rod member when said rod member is moved towards said protracted unstressed position.

19. A surgical apparatus as recited in claim 18, further comprising actuation means for remotely moving said reciprocal rod member relative to said tubular member.

20. A surgical apparatus as recited in claim 19, wherein said actuation means comprises an axial control shaft coupled to a proximal end of said rod member.

21. A surgical apparatus as recited in claim 18, wherein said distal end portion of said tubular member is formed of a thermoplastic polyurethane material.

22. A surgical apparatus as recited in claim 21, wherein said thermoplastic polyurethane material has a glass transition temperature of between about 20° C. and 40° C.

23. A surgical apparatus as recited in claim 18, wherein said reciprocal rod member is formed of a super elastic material.

24. A surgical apparatus as recited in claim 18, wherein said reciprocal rod member is formed of a shape memory alloy.

25. A surgical apparatus as recited in claim 18, wherein said tubular member is dimensioned and configured for endoscopic utilization.

26. A surgical apparatus as recited in claim 18, wherein said distal end portion has a substantially arcuate configuration when said reciprocal rod member is in said protracted position.

27. A surgical apparatus comprising:
   a) a tubular body having a first substantially tractable distal portion formed of a thermoplastic material and a second substantially firm proximal portion; and
   b) a reciprocal rod member having a preformed configuration and formed from a super elastic material disposed entirely within said tubular body and remotely movable in a longitudinal direction between a first deformed position spaced from said distal portion and a second protracted position disposed within said distal portion and wherein said distal portion conforms to said preformed configuration of said reciprocal rod member when said rod member is in said protracted second position.

28. A surgical apparatus as recited in claim 27, further comprising actuation means for remotely moving said reciprocal rod member relative to said tubular body.

29. A surgical apparatus as recited in claim 27, wherein said super elastic material is a shape memory alloy.

30. A surgical apparatus as recited in claim 27, wherein said thermoplastic material is polyurethane having a glass transition temperature of between about 20° C. and 40° C.

31. A surgical apparatus as recited in claim 27, wherein said distal portion has a substantially arcuate configuration when said reciprocal rod member is in said protracted position.

32. A surgical apparatus comprising:
   a) a tubular member having a first tractable distal end portion and a second substantially firm proximal portion and defining a longitudinal axis;
   b) a reciprocal rod member having a preformed configuration disposed entirely within said tubular member and remotely movable in a longitudinal direction between a deformed retracted position spaced from said distal end portion of said tubular member and a protracted position disposed within said distal end portion, and wherein said rod member causes said distal end portion of said tubular member to conform to said preformed configuration of said reciprocal rod member when said rod member is moved towards said protracted position; and
   c) actuation means for remotely moving said reciprocal rod member relative to said tubular member to cause said tubular member to conform to said preformed configuration for effectuating retraction.

* * * * *